United States Patent [19]

Tsurumi et al.

[11] 4,328,312

[45] May 4, 1982

[54] PROCESS FOR PRODUCTION OF PEROXIDASE

[75] Inventors: Yoshihiro Tsurumi, Tokyo; Tomio Fujioka, Matsudo; Toshio Matsuzaki; Hidechika Wakabayashi, both of Tokyo, all of Japan

[73] Assignee: Mitsubishi Gas Chemical Company, Inc., Tokyo, Japan

[21] Appl. No.: 138,978

[22] Filed: Apr. 10, 1980

[30] Foreign Application Priority Data

Apr. 11, 1979 [JP]   Japan .................................. 54/43864
Jan. 24, 1980 [JP]   Japan .................................. 55/7207

[51] Int. Cl.³ .............................................. C12N 9/08
[52] U.S. Cl. ...................................... 435/192; 435/911
[58] Field of Search ................................ 435/192, 911

[56] References Cited

U.S. PATENT DOCUMENTS 3,734,831   5/1973   Hulme ................................ 435/209

OTHER PUBLICATIONS

Koenigs, Article in Phytopathology, vol. 62, pp. 100–110, (1972).

*Primary Examiner*—Lionel M. Shapiro
*Attorney, Agent, or Firm*—Craig and Antonelli

[57] ABSTRACT

Peroxidase, which is an enzyme having a catalytic effect on oxidation by hydrogen peroxide and known to be found in vegetables such as horseradish or Japanese radish, is produced according to a biological process using a microorganism belonging to the genus Myrothecium and capable of producing a peroxidase, for example, *Myrothecium gramineum* 38-3, 46-2 and 283-2, and *Myrothecium verrucaria* IFO 6113 and IFO 6133.

15 Claims, 10 Drawing Figures

TREATMENT

PROCESS FOR PRODUCTION OF PEROXIDASE

This invention relates to a process for production of peroxidase. More particularly, this invention relates to a process for producing microbiologically peroxidase.

Peroxidase is an enzyme which has a catalytic effect on oxidation of such substances as mono-amines, polyamines or others in the presence of hydrogen peroxide. Peroxidases as derived from Japanese radish and horseradish have been used respectively for various purposes. For example, they have been used as reagents for quantitative determination of substances such as glucose, alcohol and cholesterol, which are substrates in oxidation reactions by various oxidases such as glucose oxidase, alcohol oxidase and cholesterol oxidase. They are also useful for enzymes as label in the enzyme immunoassay.

Peroxidases are present widely in the vegetable kingdom and found abundantly in juices of Japanese horseradish, fig and Japanese radish. In the animal kingdom, they are contained in leucocytes and milks. There have also been known various peroxidases of microorganism origin, as exemplified by cytochrome C peroxidase contained in both bacteria and mold fungi, NAD peroxidase contained in bacteria. These peroxidases have activities different from those of peroxidases as derived from conventional horseradish and Japanese radish.

On the other hand, growth of horseradish and Japanese radish is very slow and therefore not suitable as a resource for production of peroxidase on a large scale. Thus, the present inventors have made investigations on productivity of peroxidase of various microorganisms isolated from the natural world, in order to obtain peroxidases from such microorganisms rapid in growth which can be used for enzymes as label in clinical diagnosis and immunoassay similarly as those obtained from conventional horseradish and Japanese radish. As the result, the inventors found that microorganisms belonging to the genus Myrothecium have an ability to produce peroxidase. The present invention has been accomplished based on such a finding.

The genus Myrothecium is a kind of microorganisms belonging to Fungi Imperfecti. For example, Myrothecium verrucaria is known as a microorganism capable of producing an enzyme such as cellulase (as disclosed by Japanese published examined patent application No. 2878/1965) or as a microorganism capable of producing an antibiotic such as verrucarin (as disclosed by Japanese published examined patent applications No. 5037/1970 and No. 6876/1970). Another example is Myrothecium roridum, which is known as a microorganism capable of producing an antibiotic such as roridin (as disclosed by Japanese published examined patent application No. 12276/1970). However, no peroxidase is known at all prior to disclosure of the present invention as an enzyme which can be produced from the genus Myrothecium.

The present invention provides a process for producing peroxidase, which comprises culturing a microorganism belonging to the genus Myrothecium and capable of producing peroxidase, accumulating in the cultured product the peroxidase and collecting the accumulated peroxidase.

In the accompanying drawings, FIGS. 1 to 5 show properties of one example of peroxidase prepared according to the process of the present invention (Example 5) and FIGS. 6 to 10 those of another example (Example 7);

The microorganism to be used in the present invention may be any strain of microorganisms which belongs to the genus Myrothecium and can produce peroxidases. Suitable examples of microorganisms to be used in the present invention are Myrothecium verrucaria IFO 6113 and Myrothecium verrucaria IFO 6133, and the strains isolated by the present inventors, including Myrothecium gramineum 38-3, Myrothecium gramineum 46-2 and Myrothecium gramineum 283-2. Among these microorganism strains, those isolated by the present inventors, namely Myrothecium gramineum 38-3, Myrothecium gramineum 46-2 and Myrothecium gramineum 283-2 have the microbiological properties, respectively, as shown below.

(1) GROWTH IN VARIOUS MEDIA

| Culture conditions: | Under irradiation of fluorescent lamp, at 25° to 27° C., for 2 weeks |
|---|---|
| Culture medium | Myrothecium gramineum 38 - 3 |
| Potato dextrose agar medium | Very short, white to orange myceliums grown like a mat; sporesites** shaped in dark discs of ca. 0.5 mm in diameter, with some sporesites being agglomerated to a mass of ca. 5 mm; the surface of the sporesites covered thinly with very short myceliums and surrounded by distinct marginals of white short myceliums; no pigment produced; the backside of colony being smooth with white to orange color. |
| Sabouraud's agar medium | Myceliums tinted in white to green or orange grown like a mat; the sporesites sparingly like dark dots of ca. 0.2 mm in diameter; no pigment produced; the backside of colony being smooth with brown to mud yellow color. |
| Malt extract agar medium | Myceliums tinted in white to vermilion grown like wool; the sporesites shaped in dark dots of ca. 0.5 mm in diameter and connected at some portions; most of the sporesites covered thinly with myceliums but some sporesites erupted like tar; no pigment produced; the backside of colony being smooth with vermilion to orange color. |
| Starkey's ethanol agar medium* | White myceliums grown very weakly; small spot of dark spore masses of 0.2 mm in diameter formed at several places on mycelium; no pigment produced; the backside of colony being smooth with white color. |
| Culture medium | Myrothecium gramineum 46 - 2 |
| Potato dextrose agar medium | Abundant growth of white myceliums like wool; no spore formed; no pigment produced; the backside of colony being smooth with white color. |
| Sabouraud's agar | Myceliums tinted in white to vermilion |

| | -continued |
|---|---|
| Culture conditions: | Under irradiation of fluorescent lamp, at 25° to 27° C., for 2 weeks |
| medium | grown like wool; no spore formed and the surface wrinkled; no pigment produced and the backside of colony being wrinkled with vermilion to flesh color. |
| Malt extract agar medium | Myceliums tinted in white to vermilion grown like wool; no spore formed; no pigment produced; the backside of colony being smooth with white color. |
| Starkey's ethanol agar medium | White myceliums grown very weakly; dark spore masses of ca. 0.2 mm in diameter formed at 2 to 3 places on mycelium; no pigment formed; the backside of colony being smooth with white color. |
| Culture medium | *Myrothecium gramineum* 283 - 2 |
| Potato dextrose agar medium | Substantially no growth of mycelium; dark spore masses like tar formed; spore masses having small spherical shapes of ca. 0.2 mm in diameter, some being chained in a strand; white short myceliums densely grown around the spore masses; the surface of spore masses covered thinly by very short myceliums with spore masses like tar erupted at some portions; no pigment produced; the backside of colony being smooth with white color. |
| Sabouraud's agar medium | Myceliums colored in vermilion grown like wool; no spore formed; the surface being wrinkled; brown pigment slightly secreted; the backside of colony colored in brown with wrinkles. |
| Malt extract agar medium | Myceliums tinted in white to orange grown like wool; sporesites shaped in dark discs of ca. 1 to 2 mm in diameter, slightly raised, the surface being covered thinly with myceliums; the sporesites being scattered or chained in a strand; no pigment produced; the backside of colony being smooth with orange color. |
| Starkey's ethanol agar medium | White myceliums grown very weakly; dark spore masses of ca. 0.2 mm diameter being scattered in a large number on mycelium; no pigment produced; the backside of colony being smooth. |

*Starkey's ethanol agar medium: comprising 5 ml ethanol, 1 g $K_2HPO_4$, 0.25 g $KH_2PO_4$, 0.25 g $MgSO_4 . 7H_2O$, 0.05 g $CaCl_2$, 15 g agar and 1000 ml tap water.
**Sporesites: a place where marginal hyphae are grown around spore masses inclusive.

(2) MICROSCOPIC OBSERVATION

Microscopic observation was conducted of the sporesites in the preparation for microscopic examination and in slide culture in each medium. Each strain is found to have myceliums and conidiophores densely aggregated to form sporodochium, dark masses of conidia being formed on the head portion of sporodochium. Two to four phialides at the tip of conidiophore are grown in a whorl like a fork, the cells being cylindrically shaped with sizes of ca. $15\mu \times 2\mu$. The conidium is narrowly fusoid or lenticular, being relatively pointed and protruded at one end, and relatively rounded at the other end. The conidia are hyaline with two to five oil droplets and have sizes of $7.5-12.5\mu \times 2-3\mu$, mostly of about $10\mu \times 2.5\mu$. When they are stained by 10% ammoniacal solution of erythrosin, there is observed a fantailed appendage at one end of the conidium.

(3) PHYSIOLOGICAL PROPERTIES

Each strain has similar properties, the pH range enabling growth being 4 to 10, optimum pH range 5 to 9; growth temperature 10° to 37° C., preferably 20° to 32° C.

These strains are specific in forming sporodochium and in forming spore masses like dark tar and therefore can be identified as belonging to the genus Myrothecium. According to Mycological Papers No. 130, written by Margaret Tulloch, published on Oct. 18, 1972, the characteristic forms and sizes of conidium are best identical with those of the *Myrothecium gramineum*. Thus, all of these strains are identified by the present inventors as *Myrothecium gramineum* and they are named as *Myrothecium gramineum* 38-3, *Myrothecium gramineum* 46-2 and *Myrothecium gramineum* 283-2, respectively. All of these strains were isolated from the soil. *Myrothecium gramineum* 38-3 is deposited as FERM-P No. 4890, *Myrothecium gramineum* 46-2 as FERM-P No. 4891 and *Myrothecium gramineum* 283-2 as FERM-P No. 4892 at Institute of Fermentation Research, Agency of Industrial Science and Technology, in Japan.

For culture of the strains to be used in the present invention, spores, myceliums or pre-cultured broth of the strain are inoculated in a liquid medium or a solid medium to be cultured therein. When a liquid medium is used, there may be used as a carbon source saccharides such as glucose, saccharose, fructose, lactose, maltose, arabinose, mannose, rhamnose, starch and molasses, sugar alcohols such as mannitol and sorbitol, alcohols such as ethanol, glycerine, etc., organic acids such as malic acid, citric acid, succinic acid, etc. or salts thereof. As a nitrogen source, there may be employed a natural nitrogen source such as peptone, yeast extract, malt extract, meat extract, casamino acids (trade mark) and corn steep liquor, etc. an organic nitrogen source such as amino acids, urea, etc. and an inorganic nitrogen source such as sodium nitrate, ammonium nitrate, ammonium sulfate, etc. If necessary, there may also be added inorganic salts such as potassium phosphate, magnesium sulfate, iron sulfate, copper sulfate, potassium iodide, etc., minute nutrient sources such as vitamins, amino acids, peptone, yeast extract, malt extract, meat extract, casamino acids, etc. and surfactants such as sorbitan acid esters, polyoxyethylene sorbitan monooleate, etc. Any of these components may be added in any desired concentration, so long as it does not interfere with the growth of the microorganism. In practical applications, the carbon source may be added generally in an amount of 0.1 to 10% by weight, preferably 1 to 4% by weight, and the nitrogen source in an amount of 0.01 to 2% by weight, preferably 0.2 to 1% by weight. While adjusting the pH of the medium at 4 to 11, preferably 5 to 9, and maintaining the culture temperature at 15° to 37° C., preferably 20° to 32° C., culture may be conducted according to aeration-agitating culture, shaking culture or stationary culture.

When a solid medium is used, culture is conducted at 15° to 37° C., preferably at 20° to 32° C., for 3 to 10 days, using wheat bran, rice hulls, rice bran, etc. In this case, if necessary, there may also be added a carbon source, a nitrogen source, an inorganic salt or a minute nutrient source in the medium.

As the result of culture as described above, peroxidase is accumulated in the cultured product. The cultured product herein means the microorganism cells and/or the culture medium (culture supernatant or culture filtrate) after culture. When a liquid medium is used, peroxidase can be collected from the culture broth in the manner as described below.

After completion of culture, microorganism cells and insolubles are removed from the culture broth by such solid-liquid separation means as centrifugation or filtration to obtain culture supernatant and culture filtrate, respectively, as crude enzyme solution. Furthermore, the peroxidase contained in the microorganism cells can be recovered as crude enzyme solution which is obtained by destroying the cells by such a means as grinding or ultrasonic waves, followed by extraction of the enzyme. Alternatively, the crude enzyme solution may also be obtained by removing insolubles after destroying the microorganism cells by ultrasonic treatment, etc. The thus obtained crude enzyme solution may be subjected to purification according to such a conventional enzyme purification method as organic solvent fractionation, ammonium sulfate fractionation, dialysis, isoelectric point precipitation and column chromatography, or a combination thereof to give purified peroxidase.

When a solid medium is used, water is added to the solid medium containing the microorganism cells and insolubles are removed from the mixture as it is or after destroying the microorganism cells by ultrasonic treatment or other methods to obtain crude enzyme solution. From this crude enzyme solution, there can also be obtained purified peroxidase according to the method as described above.

In the present invention, the activity of peroxidase is measured according to the method of R. Bartha and L. Bordeleau (Soil. Biol. Biochem. 1, 139, 1969). That is, to 2.5 ml of 0.05 M phosphate buffer (pH 6.0), there are added 0.3 ml of an enzyme solution or a culture broth, of which activity is to be measured, and 0.05 ml of 0.5% methanolic solution of o-dianisidine. To the resultant mixture is further added 0.3 ml of 0.06% hydrogen peroxide in buffer, and the reaction is carried out at 30° C. for 10 minutes. After the reaction, 1 ml of 1.5% sodium azide in buffer is added to the reaction mixture. Absorbance of the resultant mixture at 460 nm is measured to give the reaction value. Separately, as "Control", the reaction is conducted in the same manner except for using 0.3 ml of buffer in place of 0.06% hydrogen peroxide in buffer, followed by measurement of absorbance at 460 nm to give the control value. The unit (U) of the peroxidase activity is represented in terms of the quantity of an enzyme which oxidizes 1μ mole of o-dianisidine in one minute, and the peroxidase activity (U/ml) of an enzyme solution or a culture broth is determined by $0.122 \times O.D._{460} \times$ (degree of dilution of enzyme solution or culture broth). In the above formula, $O.D._{460}$ is the reaction value minus the control value. In the above description about the measurement of activity, the term "buffer" means "0.05 M phosphate buffer (pH 6.0)".

The peroxidase obtained by the present invention has the properties as shown below.

(1) ACTION

In the presence of hydrogen peroxide, various compounds are catalytically oxidized:

wherein $AH_2$ and A indicate hydrogen donor and hydrogen donor oxidized, respectively.

(2) SUBSTRATE SPECIFICITY

The present of enzyme has a very specific action on hydrogen peroxide.

(3) SPECIFICITY FOR HYDROGEN DONORS

Table 1 shows the specificities of the present enzyme for various hydrogen donors:

TABLE 1

| Hydrogen donor | Strength of action |
| --- | --- |
| o-dianisidine | ++++ |
| dimethyl-p-phenylene-diamine hydrochlorine | ++++ |
| pyrogarol | +++ |
| m-phenylenediamine hydrochloride | +++ |
| p-anisidine | +++ |
| guaiacol | ++ |
| aniline | ++ |
| p-amino benzoic acid | ++ |
| catechol | ++ |
| hydroquinone | + |
| resorcin | + |

(4) REACTIVE PH AND RELATIVE ACTIVITY

Figure 1:
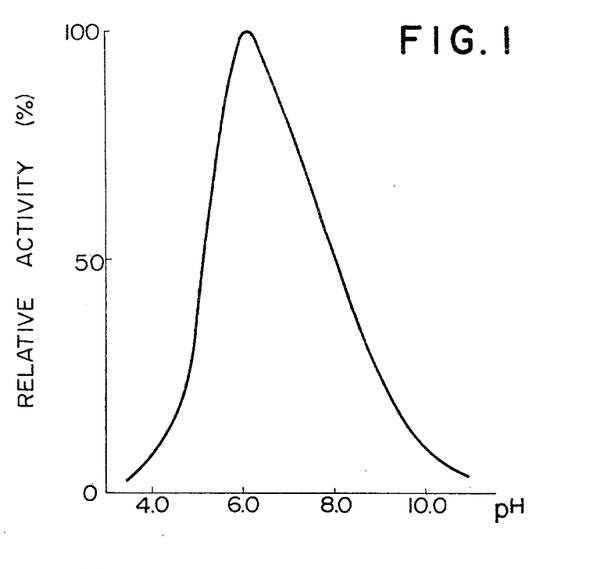
FIG. 1 and FIG. 6 are graphs indicating the relation between the reaction pH and relative activity of enzyme.
Figure 6:
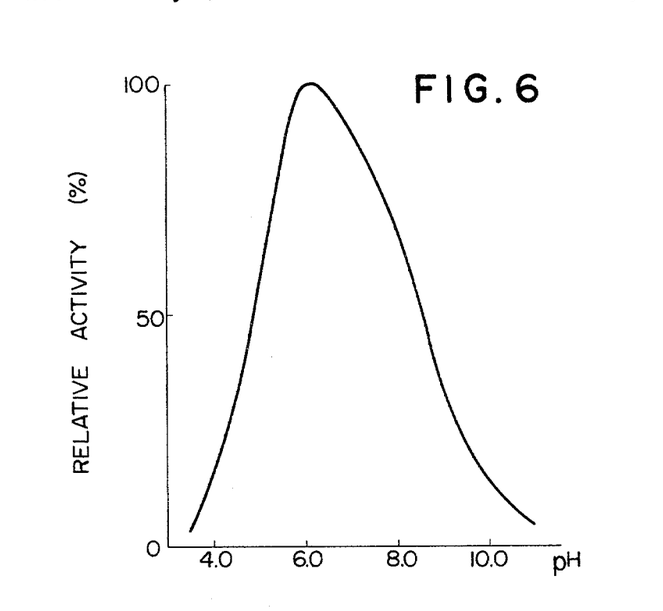

Activity of peroxidase is measured according to the same method as described above except that there are employed 2.7 ml of buffer having various pH values and 0.1 ml of an enzyme solution [an enzyme sample dissolved in 0.05 M phosphate buffer (pH 6.0) to 0.212 U/ml] in place of 2.5 ml of 0.05 M phosphate buffer (pH 6.0) and 0.3 ml of the enzyme solution. The results are shown in FIG. 1 and FIG. 6. The buffers employed and pH values practiced are as follows.

| Buffer | pH |
| --- | --- |
| 0.05 M acetate buffer | 3.5, 4.0, 4.5, 5.0 |
| 0.05 M phosphate buffer | 5.5, 6.0, 6.5, 7.0, 7.5, 8.0 |
| 0.05 M carbonate buffer | 8.5, 9.0, 10.0, 11.0 |

(5) PRE-TREATMENT PH AND RELATIVE ACTIVITY (PH STABILITY)

Enzyme samples are dissolved in buffers having various pH values as shown below to an activity of 0.0450 U/ml.

| Buffer | pH |
| --- | --- |
| 0.05 M acetate buffer | 3.5, 4.0, 4.5, 5.0 |
| 0.05 M phosphate buffer | 5.5, 6.0, 6.5, 7.0, 7.5, 8.0 |
| 0.05 M carbonate buffer | 8.5, 9.0, 10.0, 11.0, 12.0, 13.0 |

Then, these solutions are maintained at 45° C. for 30 minutes, and the peroxidase activities of the treated solutions are measured. The results are shown in FIG. 2 and FIG. 7.

(6) PH CONDITIONS FOR DEACTIVATION

Figure 2:
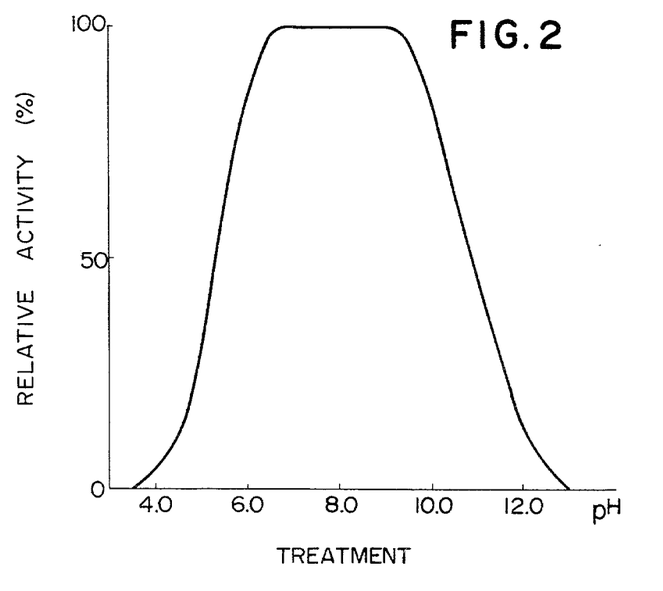
FIG. 2 and FIG. 7 are graphs indicating pH stability of enzyme.
Figure 7:
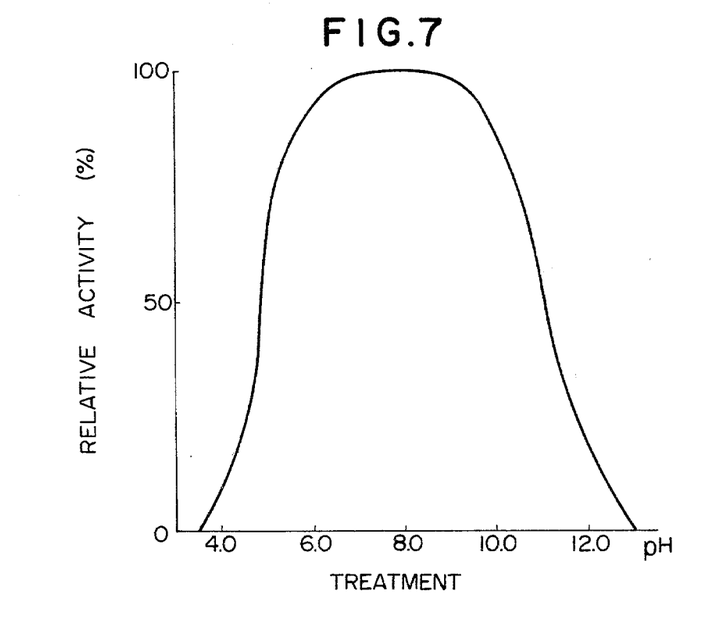

As seen from FIG. 2 and FIG. 7, the present enzyme is deactivated to 100% by the treatment at pH 3.5 and pH 13.0, at 45° C., for 30 minutes.

(7) REACTION TEMPERATURE AND RELATIVE ACTIVITY

Figure 3:
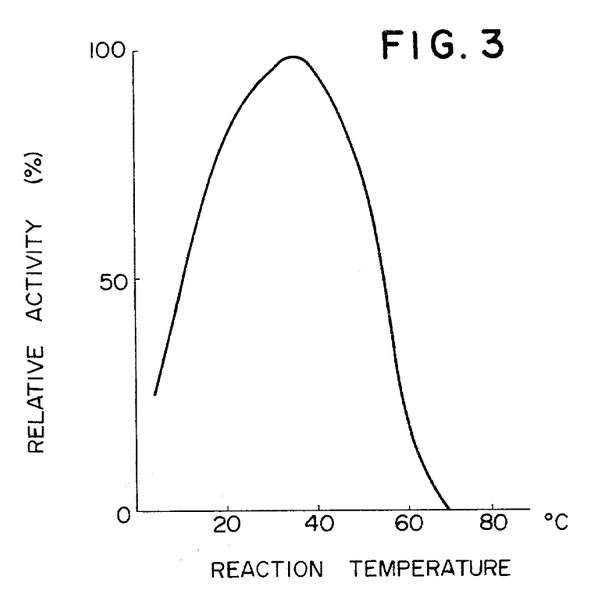
FIG. 3 and FIG. 8 are graphs indicating the relation between the reaction temperature and relative activity of enzyme.
Figure 8:
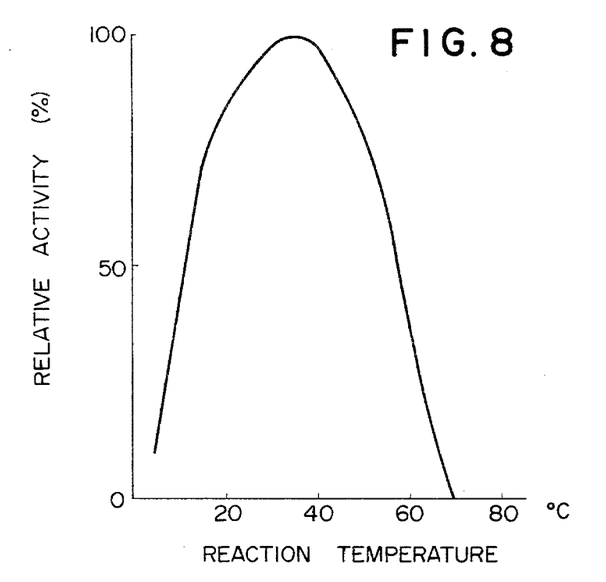

Enzyme samples are dissolved in 0.05 M phosphate buffer (pH 6.0) to an activity of 0.0480 U/ml to provide enzyme solutions, and the reaction temperature is varied from 4° to 68° C. Measurement of peroxidase activity is conducted under the same conditions as described above except the reaction temperature. The results are shown in FIG. 3 and FIG. 8.

(8) PRE-TREATMENT TEMPERATURE AND RELATIVE ACTIVITY (TEMPERATURE STABILITY)

Figure 4:
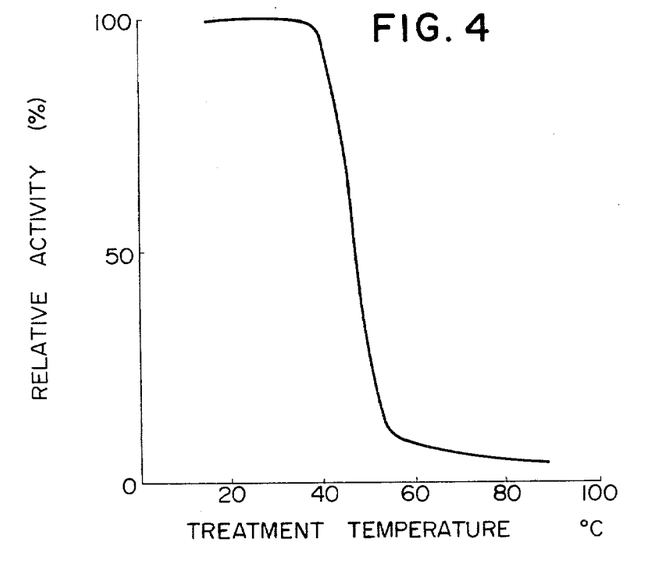
FIG. 4 and FIG. 9 are graphs indicating temperature stability of enzyme.
Figure 9:
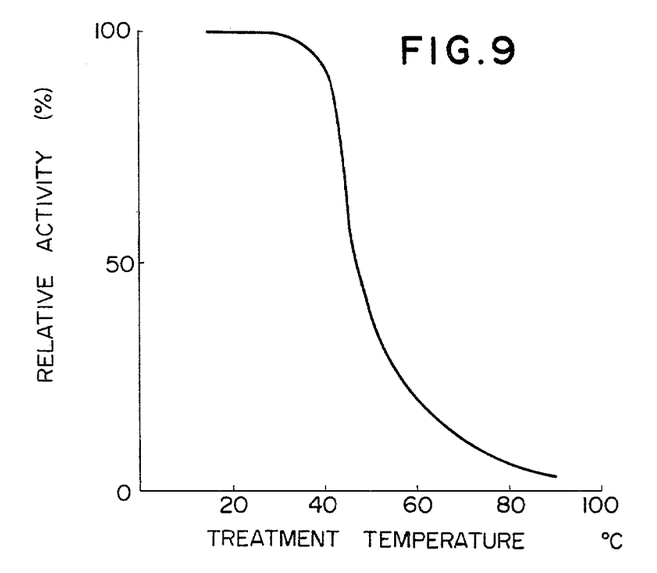

Enzyme samples are dissolved in 0.05 M phosphate buffer (pH 7.0) to an activity of 0.0422 U/ml, and the resultant solutions are maintained at various temperatures from 15° to 90° C. for 30 minutes. After the treatment, the solution is cooled on iced water for 5 minutes and thereafter subjected to measurement of the peroxidase activity. The results are shown in FIG. 4 and FIG. 9.

(9) TEMPERATURE CONDITIONS FOR DEACTIVATION

Figure 5:
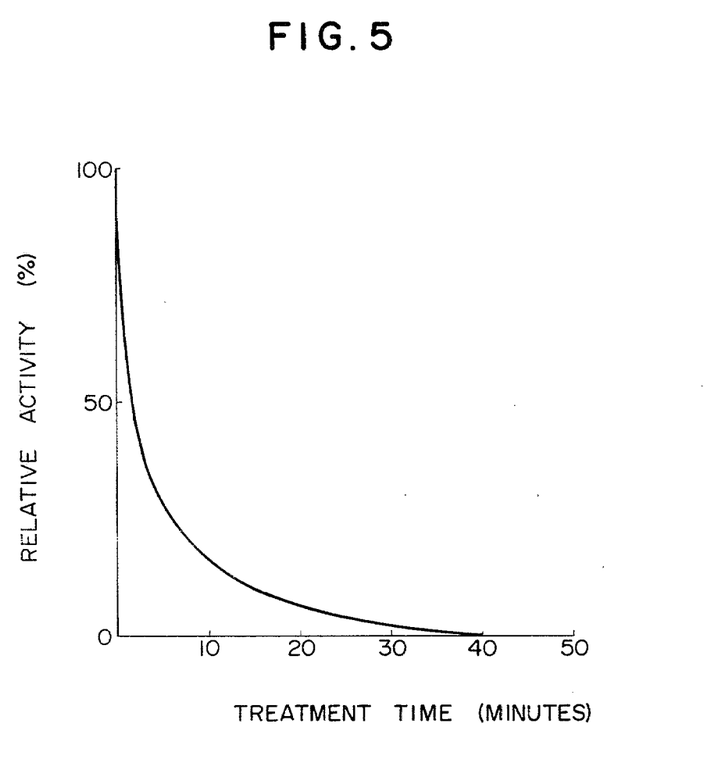
FIG. 5 and FIG. 10 are graphs indicating relation between the treatment time and relative activity of enzyme when pre-treated at 90° C.
Figure 10:
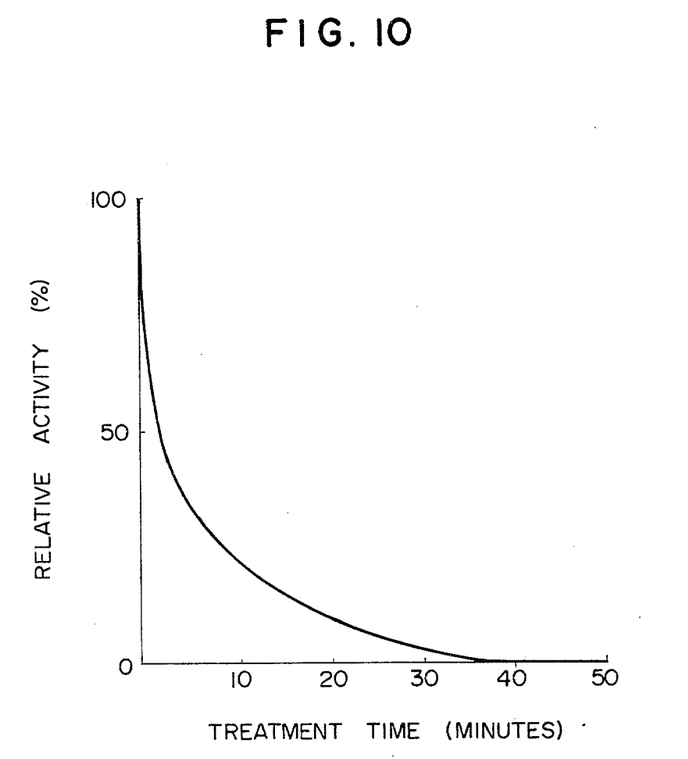

Enzyme samples are dissolved in 0.05 M phosphate buffer (pH 7.0) to an activity of 0.0389 U/ml, and the resultant solutions are subjected to pre-treatment at 90° C. for 0, 10, 20, 30, 40 and 50 minutes before measurement of peroxidase activity. The results as shown in FIG. 5 and FIG. 10. As clearly seen from FIG. 5 and FIG. 10, the present enzyme is deactivated to 100% by pre-treatment at pH 7.0, at 90° C. for 40 minutes.

(10) INHIBITION, ACTIVATION

As enzyme solutions, there are employed solutions prepared by dissolving enzyme samples in 0.05 M phosphate buffer (pH 6.0) or 0.05 M acetate buffer (pH 6.0) to an activity of 0.0296 U/ml. The peroxidase activity is measured according to the same method as described above except for using various buffers [0.05 M phosphate buffer (pH 6.0) or 0.05 M acetate buffer (pH 6.0)] containing various metallic salts or enzyme reaction inhibitors in place of 0.05 M phosphate buffer. These various metallic salts or enzyme reaction inhibitors are added to the final concentration of 2 mM. The results are shown in Table 2.

As apparently seen from Table 2, the present enzyme is activated by metallic salts such as $CaCl_2$, $BaCl_2$ and $ZnSO_4$; and inhibited by such compounds as hydroxylamine hydrochloride, $NaN_3$ and KCN. Such an inhibition is considered to be due to formation of bonding between the hemin iron of peroxidases and these compounds.

(11) MOLECULAR WEIGHT

Molecular weight is measured by the gel filtration chromatography using Sephadex G-75 Super Fine (Trade Mark: produced by Pharmacia Fine Chemicals Inc.) equilibrated with 0.05 M phosphate buffer (pH 7.0). As standard proteins, there are used ovalubumin, horseradish peroxidase, soybean trypsin inhibitor and horse cytochrome C. The elimination volume is determined by use of Blue Dextran 2000 (Trade Mark: Produced by Pharmacia Fine Chemicals Inc.). As the result, the molecular weight of the present enzyme is found to be 36,000.

In the aforesaid properties, (1) and (2) are common properties of the peroxidase obtained in the present invention. Whereas, the properties (3) et seq. will vary depending on the microorganism employed, the preparation method and test conditions. The properties as shown above are exemplary when the powdery peroxidase obtained in Example 5 and the powdery product obtained similarly as in Example 5 from the culture filtrate prepared in Example 7 are used as enzyme samples. FIG. 1 to FIG. 5 show the results obtained for the powdery product prepared in Example 5, and FIG. 6 to FIG. 10 those for the crude product obtained from the filtrate in Example 7.

The peroxidase produced according to the present invention is found to exhibit similar actions to those of conventional peroxidases derived from horseradish and Japanese radish in catalytic effect in oxidation reactions by hydrogen peroxide. It can be used as clinical diagnosis reagents and for enzymes as label in immunoassay. As compared with plants such as horseradish and Japanese radish, the microorganisms can grow more rapidly and culture thereof can very easily be carried out to a great commercial advantage.

The present invention is further illustrated with reference to the following Examples.

EXAMPLE 1

In an Erlenmeyer's flask of 300 ml capacity, there is charged 50 ml of a medium (pH 5.0) containing 2% glucose, 1% polypepton (trade mark), 0.4% $KH_2PO_4$,

TABLE 2

| Compounds added | Buffer* | Relative activity** Ex. 5 | Ex. 7 | Compounds added | Buffer* | Relative activity** Ex. 5 | Ex. 7 |
|---|---|---|---|---|---|---|---|
| NaCl | P | 96% | 100% | o-phenanthroline | P | 121% | 110% |
| KCl | P | 101 | 100 | EDTA | P | 97 | 100 |
| $MgSO_4$ | P | 102 | 100 | L-cysteine | P | 2 | 0 |
| $CaCl_2$ | A | 142 | 120 | 2-mercaptoethanol | P | 2 | 0 |
| $BaCl_2$ | A | 138 | 120 | hydroxylamine | A | 7 | 10 |
| $MnSO_4$ | A | 92 | 90 | $NaN_3$ | P | 2 | 0 |
| $CoCl_2$ | A | 102 | 100 | KCN | P | 11 | 10 |
| $NiSO_4$ | A | 107 | 100 | sodium p-chloro mercury benzoate | A | 24 | 20 |
| $ZnSO_4$ | P | 126 | 110 | | | | |
| $HgCl_2$ | P | 0 | 0 | | | | |
| $Hg(AcO)_2$ | A | 0 | 0 | no addition | P | 100 | 100 |

*Buffer:
P = 0.05 M phosphate buffer (pH 6.0)
A = 0.05 M acetate buffer (pH 6.0)
**Relative activity:
Ex. 5 = powdery product obtained in Example 5
Ex. 7 = powdery product obtained in Example 7

0.05% MgSO$_4$.7H$_2$O and 0.24 ppm CuSO$_4$.5H$_2$O, which is then subjected to sterilization at 120° C. for 10 minutes. One platinum loop of *Myrothecium gramineum* 283-2 is inoculated into the medium and stationary culture is carried out at 27° to 29° C. for 10 days. The culture broth is filtered and the peroxidase activity of the filtrate is measured to be 2.6 U/ml.

EXAMPLE 2

In a test tube of 24 mm in diameter, there is charged 10 ml of a medium (pH 5.0) containing 2% glucose and 1% Bacto-peptone (trade mark) and sterilization is effected at 120° C. for 10 minutes. One platinum loop of *Myrothecium gramineum* 283-2 is inoculated into this medium and stationary culture is carried out at 27° to 29° C. for 10 days. The peroxidase activity of the culture supernatant is found to be 1.6 U/ml. Subsequently, the culture broth is transferred as it is into a beaker of Bibrogencell-Mill (Trade Mark, produced by Edmond Behler Co., West Germany) and crushed with glass beads of 0.3 mm$\phi$ for 10 minutes. The peroxidase activity of the treated liquid is found to be 3.2 U/ml.

EXAMPLE 3

Into an Erlenmeyer's flask of 300 ml capacity, there is charged 50 ml of a medium (pH 6.0) containing 2% glucose, 1% polypepton, 0.4% KH$_2$PO$_4$, 0.05% MgSO$_4$.7H$_2$O and 0.24 ppm CuSO$_4$.5H$_2$O, followed by sterilization at 120° C. for 10 minutes. One platinum loop of *Myrothecium gramineum* 38-3 is inoculated into the medium and rotating shaking culture is carried out at 28° C. by means of a rotary shaker (200 rpm) for 10 days. The culture broth is filtered and the peroxidase activity of the filtrate is measured to be 0.8 U/ml.

EXAMPLE 4

One liter of a medium containing 2% glucose and 1% polypepton is charged into a 2-liter jar fermenter. After sterilization at 120° C. for 10 minutes, 10 ml of a pre-incubated culture broth of *Myrothecium gramineum* 46-2 is inoculated into said medium. At pH 7.0, 28° C., under aeration ratio of 1.2 V.V.M., aeration-agitating culture is carried out with stirring for 5 days. The culture broth is filtered and the peroxidase activity of the filtrate is measured to be 0.65 U/ml.

EXAMPLE 5

According to the same procedure as in Example 1, 6 liters of culture filtrate are obtained. This filtrate is concentrated to 200 ml by dialysis using a dialysis membrane of Diafilter G-10 T (Trade Mark, produced by Bioengineering Co.). Ammonium sulfate is added to the resultant concentrated solution, and the fraction precipitated at 50% saturation of ammonium sulfate are collected and dissolved in 50 ml of 0.05 M phosphate buffer (pH 7.0). This solution is subjected to dialysis through cellophane tube into the same buffer to remove ammonium sulfate. While cooling the dialyzed enzyme solution at 0° C., acetone cooled to −5° C. or lower is added thereto. The fractions precipitated at 40 to 70% acetone are collected and dissolved in 0.05 M phosphate buffer (pH 7.0). The enzyme solution is then passed into a column (2.0 cm$\phi$×75 cm) of Sephadex G-75 Super Fine (Trade Mark, Pharmacia Fine Chemicals Inc.) previously equilibrated with 0.05 M phosphate buffer (pH 7.0), and the eluate is obtained in fractions. Among the fractions of eluate, 105 ml of fractions having higher activity are collected. Ammonium sulfate is added to the collected fractions, and the fractions precipitated at 70% saturation of ammonium sulfate are collected and dissolved in 50 ml of 0.05 M phosphate buffer (pH 5.0).

The resultant solution is subjected to dialysis using celluphane tube as dialysis membrane. The inner dialyzate is lyophilized to give powder of peroxidase. The activity yield from the culture filtrate is found to be 55.0%, with specific activity of 68.2 U/mg.

EXAMPLE 6

Example 1 is repeated except that the microorganism used is changed to *Myrothecium verrucaria* IFO 6113. The culture broth is filtered and the peroxidase activity of the filtrate is measured to be 0.2 U/ml.

EXAMPLE 7

Example 1 is repeated except that the microorganism used is changed to *Myrothecium verrucaria* IFO 6133. The culture broth is filtered and the peroxidase activity of the filtrate is measured to be 0.5 U/ml.

What we claim is:

1. A process for producing a peroxidase, which comprises culturing a microorganism belonging to the genus Myrothecium and capable of producing a peroxidase in a nutrient medium, accumulating in the cultured product the peroxidase and collecting the accumulated peroxidase.

2. A process according to claim 1, wherein the microorganism belongs to *Myrothecium gramineum*.

3. A process according to claim 2, wherein the microorganism is *Myrothecium gramineum* 38-3 (FERM-P No. 4890).

4. A process according to claim 2, wherein the microorganism is *Myrothecium gramineum* 46-2 (FERM-P No. 4891).

5. A process according to claim 2, wherein the microorganism is *Myrothecium gramineum* 283-2 (FERM-P No. 4892).

6. A process according to claim 1, wherein the microorganism belongs to *Myrothecium verrucaria*.

7. A process according to claim 6, wherein the microorganism is *Myrothecium verrucaria* IFO 6113.

8. A process according to claim 6, wherein the microorganism is *Myrothecium verrucaria* IFO 6133.

9. A process according to claim 1, wherein the peroxidase has catalytic effect in oxidation reactions by hydrogen peroxide substantially the same as those possessed by the peroxidase obtained from horseradish or Japanese radish.

10. A process according to claim 1, wherein the cultured product is the microorganism cell after culture.

11. A process according to claim 1, wherein the cultured product is the culture supernatant or the culture filtrate after culture.

12. A process according to claim 1, wherein the microorganism cells separated from the culture broth are destroyed and then subjected to extraction to give a crude enzyme solution, and peroxidase is collected from said crude enzyme solution.

13. A process according to claim 1, wherein the microorganism cells in the culture broth after culture are destroyed followed by removal of insolubles, to give a crude enzyme solution, and peroxidase is collected from said crude enzyme solution.

14. A process according to claim 12 or claim 13, wherein the microorganism cells are destroyed by means of grinding or ultrasonic waves.

15. A process according to claim 11, claim 12 or claim 13, wherein peroxidase is collected from the crude enzyme solution, according to organic solvent fractionation, ammonium sulfate fractionation, dialysis, isoelectric point precipitation and/or column chromatography.

* * * * *